(12) United States Patent
Lanza et al.

(10) Patent No.: US 6,869,591 B2
(45) Date of Patent: Mar. 22, 2005

(54) PARAMAGNETIC PARTICLES THAT PROVIDE IMPROVED RELAXIVITY

(75) Inventors: Gregory Lanza, St. Louis, MO (US); Samuel A. Wickline, St. Louis, MO (US)

(73) Assignee: Barnes-Jewish Hospital, St. Louis, MO (US)

( * ) Notice: Subject to any disclaimer, the term of this patent is extended or adjusted under 35 U.S.C. 154(b) by 291 days.

(21) Appl. No.: 10/153,395

(22) Filed: May 21, 2002

(65) Prior Publication Data

US 2003/0185760 A1 Oct. 2, 2003

Related U.S. Application Data

(60) Provisional application No. 60/368,100, filed on Mar. 26, 2002.

(51) Int. Cl.$^7$ ................................................. A61B 5/055
(52) U.S. Cl. ................. 424/9.32; 424/9.322; 424/9.323
(58) Field of Search ................................ 424/9.3, 9.32, 424/9.321, 9.322, 9.323, 9.36, 450, 489

(56) References Cited

U.S. PATENT DOCUMENTS

| | | | |
|---|---|---|---|
| 5,064,636 A | 11/1991 | Li et al. | 424/9 |
| 5,120,527 A | 6/1992 | Li et al. | 424/9 |
| 5,512,294 A | 4/1996 | Li et al. | 424/450 |
| 5,571,498 A | 11/1996 | Cacheris et al. | 424/9.365 |
| 5,614,170 A | 3/1997 | Cacheris et al. | 424/9.365 |
| 5,756,069 A | 5/1998 | Torchilin et al. | 424/9.321 |
| 5,780,010 A | 7/1998 | Lanza et al. | 424/9.32 |
| 5,804,164 A | 9/1998 | Elgavish | 424/9.364 |
| 5,909,520 A | 6/1999 | Garcia | 382/303 |
| 6,010,681 A * | 1/2000 | Margerum et al. | 424/9.35 |
| 6,010,682 A | 1/2000 | Unger et al. | 424/9.361 |
| 6,045,821 A | 4/2000 | Garrity et al. | 424/450 |
| 6,088,613 A * | 7/2000 | Unger | 600/420 |
| 6,132,764 A | 10/2000 | Li et al. | 424/450 |

OTHER PUBLICATIONS

Fossheim, S.L. et al., "Paramagnetic Liposomes as MRI Contrast Agents: Influence of Liposomal Physicochemical Properties on the In Vitro Relaxivity" Magnetic Resosance Imaging 17(1):83–9 (1999).
Grant, C.W. et al., "A Liposomal MRI Contrast Agent: Phosphatidylethanolamine–DTPA" Magnetic Resonance in Medicine 11(2):236–43 (1989).

Kabalka, G.W. et al., "Gadolinium–Labeled Liposomes Containing Amphiphilic Gd–DTPA Derivatives of Varying Chain Length: Targeted MRI Contrast Enhancement Agents for the Liver" Magnetic Resonance Imaging 9(3):373–7 (1991).
Koenig, S.H., "From the Relaxivity of Gd(DTPA)2– To Everything Else" Magnetic Resonance in Medicine 22(2):183–90 (1991).
Miyamoto, M. et al., "Biodistribution of Gadolinium Incorporated in Lipid Emulsions Intraperitoneally Administered for Neutron–Capture Therapy with Tumor–Bearing Hamsters" Biological & Pharmaceutical Bulletin 22(12):1331–40 (1999).
Schwendener, R.A. et al., "A Pharmacokinetic and MRI Study of Unilamellar Gadolinium–, Manganese–, and Iron–DTPA–Stearate Liposomes as Organ–Specific Contrast Agents" Investigative Radiology 25(8):922–32 (1990).
Suga, K. et al., "Potential of Gd–DTPA–Mannan Liposome Particles as Pulmonary Perfusion MRI Contrast Agent: An Initial Animal Study" Investigative Radiology 36(3):136–45 (2001).
Tilcock, C. et al., "The Effect of Lipid Composition on the Relaxivity of Gd–DTPA Entrapped in Lipid Vesicles of Defined Size" Biochmica et Biophysica Acta 1022(2):181–6 (1990).
Tilcock, C., et al., "The Design of Liposomal Paramagnetic MR Agents: Effect of Vesicle Size Upon the Relaxivity of Surface–Incorpoated Lipophilic Chelates" Magnetic Resonance in Medicine 27(1):44–51 (1992).
Trubetskoy, V.S. et al., "Controlled Delivery of Gd–Containing Liposomes to Lymph Nodes: Surface Modification May Enhance MRI Contrast Properties" Magnetic Resonance Imaging 13(1):31–7 (1995).
Unger, E.C. et al., "Clearance of Liposomal Gadolinium: In Vivo Decomplexation" Journal of Magnetic Resonance Imaging 1(6):689–93 (1991).
Wisner, E.R. et al., "A Modular Lymphographic Magnetic Resonance Imaging Contrast Agent: Contrast Enhancement with DNA Transfection Potential" Journal of Medicinal Chemistry 40(25):3992–6 (1997).

* cited by examiner

Primary Examiner—Michael G. Hartley
(74) Attorney, Agent, or Firm—Morrison & Foerster LLP

(57) ABSTRACT

An improved contrast agent for magnetic resonance imaging comprises particles to each of which is coupled a multiplicity of chelating agents containing paramagnetic ions. In the improved agent, the position of the ion is offset from the surface of the particle so as to improve the relaxivity imparted by the contrast agent.

24 Claims, 5 Drawing Sheets

PARAMAGNETIC PARTICLES THAT PROVIDE IMPROVED RELAXIVITY

CROSS-REFERENCE TO RELATED APPLICATIONS

This application claims benefit under 35 U.S.C. § 119(e) to provisional application No. 60/368,100 filed Mar. 26, 2002, and incorporated herein by reference.

STATEMENT OF RIGHTS TO INVENTIONS MADE UNDER FEDERALLY SPONSORED RESEARCH

This work was supported in part by grants HL-59865 and CO-07121 from the National Institutes of Health and from Philips Medical Systems, Best, Netherlands. The U.S. government has certain rights in this invention.

TECHNICAL FIELD

The invention relates to improved contrast agents for magnetic resonance imaging (MRI). These agents are particles with paramagnetic ions offset from the surface.

BACKGROUND ART

Magnetic resonance imaging (MRI) has become a useful tool for diagnosis and for research. The current technology relies on detecting the energy emitted when the hydrogen nuclei in the water contained in tissues and body fluids returns to a ground state subsequent to excitation with a radio frequency. Observation of this phenomenon depends on imposing a magnetic field across the area to be observed, so that the distribution of hydrogen nuclear spins is statistically oriented in alignment with the magnetic field, and then imposing an appropriate radio frequency. This results in an excited state in which this statistical alignment is disrupted. The decay of the distribution to the ground state can then be measured as an emission of energy, the pattern of which can be detected as an image.

While the above described process is theoretically possible, it turns out that the relaxation rate of the relevant hydrogen nuclei, left to their own devices, is too slow to generate detectable amounts of energy, as a practical matter. In order to remedy this, the area to be imaged is supplied with a contrast agent, generally a strongly paramagnetic metal, which effectively acts as a catalyst to accelerate the decay, thus permitting sufficient energy to be emitted to create a detectable bright signal. To put it succinctly, contrast agents decrease the relaxation time and increase the reciprocal of the relaxation time—i.e., the "relaxivity" of the surrounding hydrogen nuclei.

Two types of relaxation times can be measured. $T_1$ is the time for the magnetic distribution to return to 63% of its original distribution longitudinally with respect to the magnetic field and the relaxivity $\rho_1$, is its reciprocal. $T_2$ measures the time wherein 63% of the distribution returns to the ground state transverse to the magnetic field. Its reciprocal is the relaxivity index $\rho_2$. In general, the relaxation times and relaxivities will vary with the strength of the magnetic field; this is most pronounced in the case of the longitudinal component.

Thus, a desirable characteristic of any contrast agents is to provide the signal with an enhanced relaxivity both for $\rho_1$ and $\rho_2$. The present invention provides such contrast agents.

There is an extensive literature regarding contrast agents which are based on chelated paramagnetic metals. For example, U.S. Pat. Nos. 5,512,294 and 6,132,764 describe liposomal particles with metal chelates on their surfaces as MRI contrast agents. U.S. Pat. Nos. 5,064,636 and 5,120,527 describe paramagnetic oil emulsions for MRI in the gastrointestinal tract. U.S. Pat. Nos. 5,614,170 and 5,571,498 describe emulsions that incorporate lipophilic gadolinium chelates, e.g., gadolinium diethylene-triamine-pentaacetic acid-bis-oleate (Gd-DTPA-BOA) as blood pool contrast agents.

U.S. Pat. No. 5,804,164 describes water-soluble, lipophilic agents which comprise particularly designed chelating agents and paramagnetic metals. U.S. Pat. No. 6,010,682 and other members of the same patent family describe lipid soluble chelating contrast agents containing paramagnetic metals which are said to be able to be administered in the form of liposomes, micelles or lipid emulsions.

Thus, in general, contrast agents may take the form of paramagnetic metals such as rare earth metals or iron mobilized in a form that permits substantial concentrations of the paramagnetic metal to be delivered to the desired imaging area.

One method for providing useful concentrations of contrast agents has been described by the present applicants in U.S. Pat. Nos. 5,780,010 and 5,909,520. A nanoparticle is formed from an inert core surrounded by a lipid/surfactant coating. The lipid/surfactant coating can then be modified to couple the particle to a chelating agent containing a paramagnetic metal. In addition, the particle can be coupled to a ligand for targeting to a specific site.

The present invention provides an improvement in the design of contrast agents whereby the relaxivity of the signal can be enhanced dramatically.

DISCLOSURE OF THE INVENTION

The present invention concerns improved contrast agents with enhanced signal relaxivities wherein this result is achieved by delivering the paramagnetic metal in high concentration in such a way as to provide increased access to the hydrogen nuclei in the surrounding medium. The agents of the invention employ particles, preferably, but not necessarily, in a liquid emulsion, wherein the particles are coupled to a multiplicity of chelating agents, said chelating agents containing a paramagnetic ion. Rather than being coupled close to the surface, the chelate is offset from the surface of the particle so as to have better access to the surrounding medium containing the hydrogen nuclei which generate the signal. The particles may also contain ligands for targeting to specific sites, may also comprise drugs, and may be formed from fluorocarbons, thus permitting $^{19}$F-MRI as a supplement.

Thus, in one aspect, the invention relates to a contrast agent for magnetic resonance imaging, which agent comprises particles, said particles coupled to a chelator containing a paramagnetic ion which is positioned offset from the surface of the particles, so as to provide the paramagnetic ion with substantial access to water molecules in a surrounding aqueous liquid.

In other aspects, the invention relates to methods to prepare the agents of the invention and methods to use them in magnetic resonance imaging techniques.

MODES OF CARRYING OUT THE INVENTION

Figure 1:
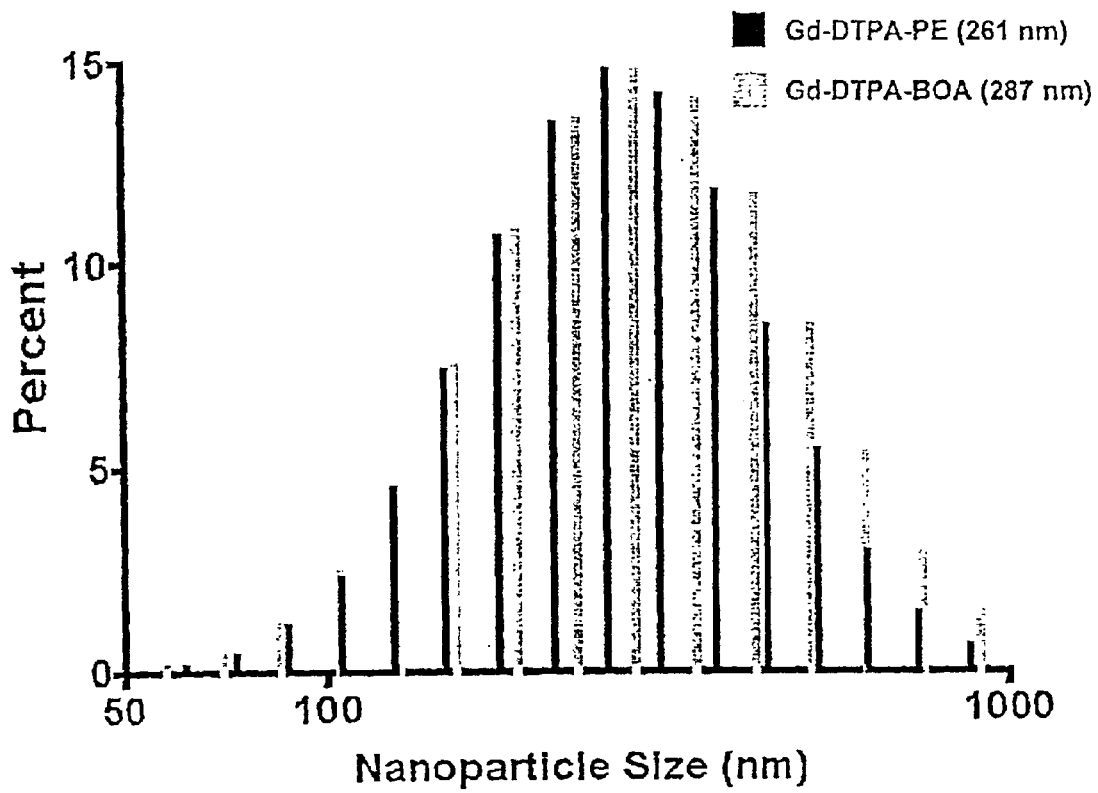
FIG. 1 shows the size distribution of nanoparticles wherein a gadolinium complex is coupled through phosphatidyl ethanolamine (Gd-DTPA-PE) and for nanoparticles wherein a gadolinium chelate is coupled through bis oleate (Gd-DTPA-BOA).

The agents of the invention, useful in MRI, comprise particles to which a multiplicity of chelating agents containing paramagnetic ions is bound. The particles will often form an emulsion or suspension in a liquid medium and can be delivered to the area to be imaged. As stated above, the invention is directed to a method to improve relaxivity by offsetting the chelating agent which contains the paramagnetic ion from the particle to which it is bound. This improvement and concept are applicable to particle-borne chelating agents in general, including liposomes, micelles, particles formed from lipoproteins, fullerenes, polymeric particles, such as latex, proteinaceous particles, or particles formed from any other basic structure such as lipids, including oils and vitamins, carbohydrates, inorganic materials, particles designated as nanospheres or microspheres, and particles which include gaseous forms such as microbubbles. The particles need not be composed of a single component, but can include mixtures, for example synthetic oils, vitamins, halogenated chemicals, and the like. Any particulate carrier can serve as the carrier for compositions which apply the methods of the invention.

In the particles of the invention, the coupling is such that the paramagnetic ion is offset from the surface of the particle at a distance, preferably, of at least 5 or 10 Å. Preferably the average distance at which the paramagnetic ion is found from the surface is between about 5–100 Å, preferably about 10–50 Å, and more preferably about 10–20 Å.

As used herein, the "surface" of the particle means the outer limit of the material comprising the particle at the location at which the chelator is coupled. Overall, the mean diameter of the particle itself is compared to the mean distance from the center where the paramagnetic ions reside. This should be at least a 5 Å difference preferably at least 10 Å.

The degree of offset can also be defined in terms of the resultant impact on the relaxivity imparted by the offset. The imparted relaxivity is dependent on the strength of the magnetic field; the relaxivity on a per particle basis is, of course, determined in part by the number of paramagnetic ions associated with the particle itself. At the arbitrarily chosen magnetic field strength of 0.47 T, the offset will be sufficient to enhance the relaxivity on a per ion basis at least 1.2 fold, preferably 1.5 fold, and more preferably 2.0 fold for $\rho_1$ and in similar amounts for $\rho_2$. At the arbitrarily chosen magnetic field of 1.5 T, the offsets will enhance these relaxivities by similar factors. At 4.7 T, preferably the enhancement of $\rho_1$ is at least 1.5 fold, preferably 2 fold and the enhancement of $\rho_2$ is at least two fold and preferably three fold, again, on a per ion basis. In terms of units of relaxivity per se, the offset is such that the value for $\rho_1$ in $(s*mM)^{-1}$ at 0.47 T is at least 20, and preferably 25, more preferably 30; at 1.5 T, these values would be at least 20, and preferably 30, and at 4.7 T, at least 10, and preferably 14. For $\rho_2$, the corresponding values at 0.47 T would be at least 20, preferably 30, and more preferably 35; at 1.5 T, at least 20, preferably 30; and at 4.7 T, at least 20, more preferably 40, and most preferably 60.

As applicants are able to apply to the particles a multiplicity of chelators containing paramagnetic ions, considerably higher relaxivities can be obtained on a per particle basis. The fold increase in $\rho_1$ and $\rho_2$ on a per particle basis is, of course, similar to that with respect to the fold increase on a per ion basis. Applicants, however, have been able to achieve values of $\rho_1$ in units of $(s*mM)^{-1}$ on a per particle basis at 0.47 T, of at least $1.8 \times 10^6$, preferably $2.0 \times 10^6$, and more preferably $2.5 \times 10^6$. At 1.5 T, these values are similar and at 4.7 T, relaxivity values for $\rho_1$ are at least $8 \times 10^5$, preferably $1 \times 10^6$, more preferably $1.1 \times 10^6$.

For $\rho_2$ at 0.47 T, the relaxivity is preferably at least $2 \times 10^6$, more preferably $2.5 \times 10^6$, and more preferably $3 \times 10^6$ in these units. At 1.5 T, the values for $\rho_2$ are at least $1.6 \times 10^6$, preferably $2.5 \times 10^6$, and more preferably $3 \times 10^6$. At 4.7 T, $\rho_2$ is at least $3 \times 10^6$, more preferably $4 \times 10^6$, and more preferably $5 \times 10^6$.

The offsetting is accomplished by spacing the dentate portion of the chelate through a tether to the surface of the particle. In one embodiment, the surface is coated with a lipophilic material and the tether is anchored into the coating through a hydrophobic moiety such as one or more aliphatic hydrocarbon chains. In one preferred embodiment, the particles themselves can be described generally as nanoparticles having an inert core surrounded by a coating to which any desired materials can be coupled. In the agent of the invention, these materials must include the chelate containing the paramagnetic ion.

With respect to these preferred particles, the inert core can be a vegetable, animal or mineral oil, but is preferably a fluorocarbon compound—perfluorinated or otherwise rendered additionally inert. Mineral oils include petroleum derived oils such as paraffin oil and the like. Vegetable oils include, for example, linseed, safflower, soybean, castor, cottonseed, palm and coconut oils. Animal oils include tallow, lard, fish oils, and the like. Many oils are triglycerides.

Fluorinated liquids are particularly useful as cores. These include straight chain, branched chain, and cyclic hydrocarbons, preferably perfluorinated. Some satisfactorily fluorinated, preferably perfluorinated organic compounds useful in the particles of the invention themselves contain functional groups. However, perfluorinated hydrocarbons are preferred. The nanoparticle core may comprise a mixture of such fluorinated materials. Typically, at least 50% fluorination is desirable in these inert supports. Preferably, the inert core has a boiling point of above 20° C., more preferably above 30° C., still more preferably above 50° C., and still more preferably above about 90° C.

Thus, the perfluoro compounds that are particularly useful in the above-described nanoparticle aspect of the invention include partially or substantially or completely fluorinated compounds. Chlorinated, brominated or iodinated forms may also be used. A detailed list of compounds useful as nanoparticle cores is included after the Examples below.

With respect to the coating on the nanoparticles in this aspect, the relatively inert core is provided with a lipid/surfactant coating that will serve to anchor the desired moieties to the nanoparticle itself. If an emulsion is to be formed, the coating typically should include a surfactant.

Typically, the coating will contain lecithin type compounds which contain both polar and non-polar portions as well as additional agents such as cholesterol. Typical materials for inclusion in the coating include lipid surfactants such as natural or synthetic phospholipids, but also fatty acids, cholesterols, lysolipids, sphingomyelins, tocopherols, glucolipids, stearylamines, cardiolipins, a lipid with ether or ester linked fatty acids, polymerized lipids, and lipid conjugated polyethylene glycol. Other surfactants are commercially available.

The foregoing may be mixed with anionic and cationic surfactants.

Fluorochemical surfactants may also be used. These include perfluorinated alcohol phosphate esters and their salts; perfluorinated sulfonamide alcohol phosphate esters and their salts; perfluorinated alkyl sulfonamide alkylene quaternary ammonium salts; N,N-(carboxyl-substituted lower alkyl) perfluorinated alkyl sulfonamides; and mixtures thereof. As used with regard to such surfactants, the term "perfluorinated" means that the surfactant contains at least one perfluorinated alkyl group. A detailed list of surfactants, including fluorinated surfactants that can be used in the coating, is found in the appendix after the Examples.

Typically, the lipids/surfactants are used in a total amount of 0.01–5% by weight of the nanoparticles, preferably 0.1–1% by weight. In one embodiment, lipid/surfactant encapsulated emulsions can be formulated with cationic lipids in the surfactant layer that facilitate the adhesion of nucleic acid material to particle surfaces. Cationic lipids include DOTMA, N-[1-(2,3-dioleoyloxy)propyl]-N,N,N-trimethylammoium chloride; DOTAP, 1,2-dioleoyloxy-3-(trimethylammonio)propane; and DOTB, 1,2-dioleoyl-3-(4'-trimethyl-ammonio)butanoyl-sn-glycerol may be used. In general the molar ratio of cationic lipid to non-cationic lipid in the lipid/surfactant monolayer may be, for example, 1:1000 to 2:1, preferably, between 2:1 to 1:10, more preferably in the range between 1:1 to 1:2.5 and most preferably 1:1 (ratio of mole amount cationic lipid to mole amount non-cationic lipid, e.g., DPPC). A wide variety of lipids may comprise the non-cationic lipid component of the emulsion surfactant, particularly dipalmitoylphosphatidylcholine, dipalmitoylphosphatidyl-ethanolamine or dioleoylphosphatidylethanolamine in addition to those previously described. In lieu of cationic lipids as described above, lipids bearing cationic polymers such as polyamines, e.g., spermine or polylysine or polyarginine may also be included in the lipid surfactant and afford binding of a negatively charged therapeutic, such as genetic material or analogues there of, to the outside of the emulsion particles.

In addition to the above-described preferred embodiment, a multiplicity of other particulate supports may be used in carrying out the method of the invention. In other embodiments, for example, the particles may be liposomal particles. The literature describing various types of liposomes is vast and well known to practitioners. As the liposomes themselves are comprised of lipid moieties, the above-described lipids and surfactants are applicable in the description of moieties contained in the liposomes themselves. These lipophilic components can be used to couple to the chelating agent in a manner similar to that described above with respect to the coating on the nanoparticles having an inert core. Micelles are composed of similar materials, and this approach to coupling desired materials, and in particular, the chelating agents applies to them as well. Solid forms of lipids may also be used.

In another example, proteins or other polymers can be used to form the particulate carrier. These materials can form an inert core to which a lipophilic coating is applied, or the chelating agent can be coupled directly to the polymeric material through techniques employed, for example, in binding affinity reagents to particulate solid supports. Thus, for example, particles formed from proteins can be coupled to tether molecules containing carboxylic acid and/or amino groups through dehydration reactions mediated, for example, by carbodiimides. Sulfur-containing proteins can be coupled through maleimide linkages to other organic molecules which contain tethers to which the chelating agent is bound. Depending on the nature of the particulate carrier, the method of coupling so that an offset is obtained between the dentate portion of the chelating agent and the surface of the particle will be apparent to the ordinarily skilled practitioner.

In all cases, to serve as MRI contrast agents, the particles are coupled through the required spacer to a chelator in which a transition metal is disposed. Typical chelators are found in the patent documents cited in the Background section above, and include porphyrins, ethylenediaminetetraacetic acid (EDTA), diethylenetriamine-N,N,N',N'',N''-pentaacetate (DTPA), 1,4,10,13-tetraoxa-7,16-diazacyclooctadecane-7 (ODDA), 16-diacetate, N-2-(azol-1 (2)-yl)ethyliminodiacetic acids, 1,4,7,10-tetraazacyclododecane-N,N',N'',N'''-tetraacetic acid (DOTA), 1,7,13-triaza-4,10,16-trioxacyclo-octadecane-N, N',N''-triacetate (TTTA), tetraethylene glycols,1,5,9-triazacyclododecane-N,N',N'',-tris(methylenephosphonic acid (DOTRP),N,N',N''-trimethylammonium chloride (DOTMA) and analogues thereof.

Suitable paramagnetic metals include a lanthanide element of atomic numbers 58–70 or a transition metal of atomic numbers 21–29, 42 or 44, i.e., for example, scandium, titanium, vanadium, chromium, manganese, iron, cobalt, nickel, copper, molybdenum, ruthenium, cerium, praseodymium, neodymium, promethium, samarium, europium, gadolinium, terbium, dysprosium, holmium, erbium, thulium, and ytterbium, most preferably Gd(III), Mn(II), iron, europium and/or dysprosium.

According to the invention, the chelating moiety is coupled to the particle through a spacer or tether which may be an aliphatic chain, a peptide, a polyethylene glycol polymer, or any suitable spacing molecule. One end of the spacer is bound, preferably covalently, to the dentate portion of the chelating agent; the other is anchored to the particle. The coupling to the particle can be covalent or the spacer may be anchored through ionic bonding, hydrogen bonding or van der Waals forces. When the particle surface comprises a lipid surface, particularly preferred anchoring moieties are the hydrocarbon side chains of phosphatides or other di-substituted glycerol derivatives.

By appropriately coupling the chelating agents, substantial numbers of chelators and paramagnetic ions can be coupled to the particles. Typically, the particles will be coupled to at least 10,000 chelators and/or paramagnetic ions, preferably 20,000 chelators and/or paramagnetic ions, more preferably 50,000 chelators and/or paramagnetic ions, more preferably at least 70,000 chelators and/or paramagnetic ions and more preferably at least 100,000 chelators and/or paramagnetic ions.

As set forth above, the tether is such that an offset is obtained sufficient to confer the relaxivity values described above, and spacing the paramagnetic ion from the surface of the particle as described.

While the particles of the invention are required to comprise a multiplicity of paramagnetic ions coupled through chelating agents, additional components may also be coupled to these particles. Especially advantageous for use of the contrast agents in some applications of MRI is the inclusion of a ligand which is a specific binding partner for a target on a tissue desired to be imaged. It may also be desirable to provide a biologically active substance and this may he included as well.

Thus, in addition to the chelated paramagnetic metal ion, the particles may also be coupled to ligands for targeting and/or biologically active molecules. It is possible also to include among the components coupled to the particles bearing the chelated paramagnetic ion, radionuclides for use in treatment or diagnosis.

Suitable biologically active materials include therapeutics such as antineoplastic agents, hormones, anticoagulants, and other pharmaceuticals, representative examples of which are listed in the appendix after the Examples.

In one important embodiment of the invention, the particles containing the offset contrast ion are targeted to a desired destination; however, this is not the case for all purposes. For example, the contrast agents of the invention are useful in blood pool contexts or in the gastrointestinal tract where specific localization is unnecessary. However, the particles may also be targeted to specific organs or types of tissue, including fibrin clots, liver, pancreas, neurons, or any tissue characterized by particular cell surface or other ligand-binding moieties. In order to effect this targeting, a suitable ligand is coupled to the particle directly or indirectly. An indirect method is described in U.S. Pat. No. 5,690,907, incorporated herein by reference. In this method, the lipid/surfactant layer of a nanoparticle is biotinylated and the targeted tissue is coupled to a biotinylated form of its specific binding ligand. The biotinylated nanoparticle then reaches its target through the mediation of avidin which couples the two biotinylated components.

In a preferred method, the specific ligand itself is coupled directly to the particle, preferably but not necessarily, covalently. Thus, in such "direct" coupling, a ligand which is a specific binding partner for a target contained in the desired location is itself linked to the components of the particle, as opposed to indirect coupling where a biotinylated ligand resides at the intended target. Such direct coupling can be effected through linking molecules or by direct interaction with a surface component. Homobifunctional and heterobifunctional linking molecules are commercially available, and functional groups contained on the ligand can be used to effect covalent linkage. Typical functional groups that may be present on targeting ligands include amino groups, carboxyl groups and sulfhydryl groups. In addition, crosslinking methods, such as those mediated by glutaraldehyde could be employed. For example, sulfhydryl groups can be coupled through an unsaturated portion of a linking molecule or of a surface component; amides can be formed between an amino group on the ligand and a carboxyl group contained at the surface or vice versa through treatment with dehydrating agents such as carbodiimides. A wide variety of methods for direct coupling of ligands to components of particles in general and to components such as those found in a lipid/surfactant coating in one embodiment are known in the art. The foregoing discussion is non-comprehensive. In a specific case which employs aptamers, it may be advantageous to couple the aptamer to the nanoparticle by the use of a cationic surfactant as a coating to the particles.

The targeting agent itself may be any molecule which is specific for an intended target. Commonly, such a ligand may comprise an antibody or portion thereof, an aptamer designed to bind the target in question, a known ligand for a specific receptor such as an opioid receptor binding ligand, a hormone known to target a particular receptor, a peptide mimetic and the like. Certain organs are known to comprise surface molecules which bind known ligands; even if a suitable ligand is unknown, antibodies can be raised and modified using standard techniques and aptamers can be designed for such binding.

Antibodies or fragments thereof are preferred targeting agents because of their capacity to be generated to virtually any target, regardless of whether the target has a known ligand to which it binds either natively or by design. Standard methods of raising antibodies, including the production of monoclonal antibodies are well known in the art and need not be repeated here. It is well known that the binding portions of the antibodies reside in the variable regions thereof, and thus fragments of antibodies which contain only variable regions, such as $F_{ab}$, $F_v$, and $scF_v$ moieties are included within the definition of "antibodies." Recombinant production of antibodies and these fragments which are included in the definition are also well established. If the imaging is to be conducted on human subjects, it may be preferable to humanize any antibodies which serve as targeting ligands. Techniques for such humanization are also well known.

Thus, in summary, the contrast agents of the invention mandatorily comprise particulate carriers which are coupled to a multiplicity of chelating agents containing paramagnetic metal ions in such a manner that the paramagnetic metal ion is offset from the surface of the particle so as more effectively to contact the surrounding medium containing the hydrogen nuclei that emit signals under the conditions of the MRI image construction. The offset is such that the average distance of the paramagnetic ion from the surface is of the order of 10 Å and at such a distance that the relaxivity of the surrounding hydrogen ions is enhanced, for example, at least 1.5 fold as compared to particles wherein the paramagnetic ion is directly attached to the surface, preferably enhanced 2-fold, and more preferably enhanced at least 2.5 fold, and still more preferably enhanced at least 6 fold, or even 10 fold. Alternatively, for example the offset distance from the surface can be judged on the basis of the ion-based relaxivity in $(s*mM)^{-1}$ as, e.g., for $\rho_1$ at least about 10, preferably 20 or 30 and up to 100 at a magnetic field of 1.5 T and $\rho_2$ at least about 20, preferably 30 or 40 and up to 100 in these units at 1.5 T; or the relaxivity on a per particle basis at least, for example, about $0.5 \times 10^6$, preferably $1.5 \times 10^6$ and up to $15 \times 10^6$; $(s*mM)^{-1}$ at 1.5 T for $\rho_1$ and at least about $1.0 \times 10^6$ preferably $3.0 \times 10^6$ and up to $15 \times 10^6$ in these units for $\rho_2$. As stated above, in addition to the offset paramagnetic ions, the particles may also contain targeting moieties, bioactive agents, or radionuclides. Preferably, targeting ligands are included.

It is understood that with respect to any material comprised by the particles, a multiplicity of copies may be included. For the chelator containing a paramagnetic ion, typically, the particles contain at least 2,000 copies, typically at least 5,000, more typically at least 10,000 or 100,000 or 500,000. For targeting agents, only one or two, or several or more copies may be included. Variable numbers of drug molecules may be contained.

The precise process for preparation of the contrast agents of the invention is variable, and depends on the nature of the particulate carrier and the choice of tether or spacer molecules. As described above, solid particles which contain reactive groups can be coupled directly to the tether or spacer; lipid-based particles such as oil emulsions, solid lipids, liposomes, and the like, can include lipophilic materials containing reactive groups which may covalently, then, be coupled to linking moieties which bear the dentate portion of the chelating agent. In one particularly preferred embodiment, the process involves mixing a liquid fluorocarbon compound that forms the core of a nanoparticle and the components of a lipid/surfactant coating for that particle in an aqueous suspension, microfluidizing, and, if desired, harvesting and sizing the particles. The components to be coupled can be included in the original mixture by virtue of their initial coupling to one or more components of the lipid/surfactant coating, or the coupling to additional moieties can be conducted after the particles are formed.

A typical preparation of one preferred agent of the invention is described as follows:

The emulsion comprises perfluorocarbon (e.g., perfluorooctylbromide 40% w/v, PFOB), a surfactant co-mixture (2.0%, w/v) and glycerin (1.7%, w/v) in aqueous medium. The surfactant co-mixture may include dipalmitoylphosphatidyl choline, cholesterol, dipalmitoylphosphatidyl ethanolamine-DTPA-Gd (or may include, for example, phosphoethanolamine-N-4 $PEG_{(2000)}$-(p-maleimidophenyl) butyramide (MPB-PEG-PE) if further coupling to a targeting ligand is required) phosphatidylethanolamine, and/or sphingomyelin in varying molar ratios, which are dissolved in chloroform/methanol, evaporated under reduced pressure, dried in a 50° C. vacuum oven overnight and dispersed into water by sonication. Optionally, one or more therapeutic agents may be included. The suspension is combined with the perfluorooctaylbromide and distilled, added to deionized water, blended and then emulsified at 20,000 PSI for three minutes (S110 Microfluidics microemulsification).

For targeting, a thiolated peptidomimetic ligand is coupled to the maleimide derivatized phospholipid included in the coating in 50 mM phosphate, 10 mM EDTA buffer at pH 6.65 overnight under a nitrogen atmosphere. Alternatively, phosphoethanolamine-N-4 $PEG_{(2000)}$-(p-maleimidophenyl)butyramide (MPB-PEG-PE) may be dried into a lipid film under vacuum and the thiolated peptidomimetic ligand may be coupled to the lipid upon resuspension with in 50 mM phosphate, 10 mM EDTA buffer at pH 6.65 so as to be included in the particles upon formation.

Alternatively the ligand, such as an antibody, antibody fragment or small molecule analogue thereof (e.g., $ScF_v$) may be reacted with N-succinimidyl S-acetylthioacetate (SATA) for 30 min, dialyzed overnight, deprotected with hydroxylamine, dialyzed in oxygen free buffers, then coupled to the nanoparticles at room temperature for 2 hours. A control emulsion is prepared identically with a nonderivatized phosphatidylethanolamine substituted into the surfactant commixture and the ligand conjugation steps are omitted.

Vialed peptidomimetic emulsions are heat sterilized with neutral pH adjustment ($NaCO_3$) at 121° C. for 15 min. Nanoparticles for conjugation to antibodies are heat sterilized before coupling and ligand conjugation is completed under aseptic conditions in a laminar flow biohood. The improved nanoparticle-based contrast agents are then useful in obtaining magnetic resonance images in subjects using standard techniques for obtaining such images.

The contrast agents may be used without targeting ligands for obtaining images where homing to a site is unnecessary, such as blood pool images. However, where specific organs are to be imaged, targeted forms of the particles are preferred.

The use of perfluoro carbons as the basis for the nanoparticles in this embodiment of the invention is further advantageous in that resonance images of the $^{19}F$ contained in the particle can also be concomitantly obtained and serve to verify the translocation of the contrast agent to the desired locations in the subject.

The following examples are intended to illustrate but not to limit the invention.

Preparation A

Nanoparticle Preparation

Paramagnetic nanoparticles were produced in a modification of the procedure described by Lanza, G, et al., *Circulation* (1996) 94:3334–3340. Briefly, the emulsions comprised 40% (v/v) perfluorooctylbromide (PFOB; MMM, St. Paul, Minn.), 2% (w/v) safflower oil, 2% (w/v) of a surfactant co-mixture, 1.7% (w/v) glycerin and water representing the balance. The surfactant co-mixture included 63 mole % lecithin (Avanti Polar Lipids, Inc., Alabaster, Ala.), 15 mole % cholesterol (Sigma Chemical Co., St. Louis, Mo.), 2 mole % dipahnitoyl-phosphatidylethanolamine (Avanti Polar Lipids, Inc., Alabaster, Ala.), and 20 mole % of the paramagnetic lipophilic chelate. The lipophilic chelate was either gadolinium diethylene-triamine-pentaacetic acid-bis-oleate (Gd-DTPA-BOA; Gateway Chemical Technologies, St. Louis, Mo.) or DTPA-phosphatidylethanolamine (DTPA-PE; Gateway Chemical Technologies, St. Louis, Mo.). The surfactant components were dissolved in chloroform, evaporated under reduced pressure, dried in a 50° C. vacuum oven overnight and dispersed into water by sonication. The suspension was pre-emulsified in a blender with PFOB, safflower oil and distilled deionized water for 30 to 60 seconds and then emulsified in a M110S Microfluidics emulsifier (Microfluidics, Newton, Mass.) at 20,000 PSI for four minutes. The completed formulation was placed in crimp sealed vials and blanketed with nitrogen. Particle sizes were determined in triplicate at 37° C. with a laser light scattering submicron particle sizer (Malvern Instruments, Malvern, Worcestershire, UK).

EXAMPLE 1

Preparation of Contrast Agent

As set forth in Preparation A, Either gadolinium diethylene-triamine-pentaacetic acid-bis-oleate (Gd-DTPA-BOA; Gateway Chemical Technologies, St. Louis, Mo.) or DTPA-phosphatidylethanolamine (DTPA-PE; Gateway Chemical Technologies, St. Louis, Mo.), was included in the surfactant co-mixture at a concentration of 20 mole % of the total lipid membrane. Gadolinium chloride was added in excess proportions as a post-emulsification step to nanoparticles formulated with DTPA-PE. Unbound gadolinium was removed by dialysis on the nanoparticles against distilled deionized water (300,000 MW cut-off, Spectrum Laboratories, Rancho Dominguez, Calif.). Gadolinium-DTPA-BOA was incorporated into the surfactant lipids as the complete paramagnetic compound. Both Gd-DTPA-BOA and Gd-DTPA-PE emulsions were tested for free $Gd^{3+}$ using the arsenazo III reaction and showed no sign of unbound lanthanide.

The concentration of $Gd^{3+}$ was calculated from the reactants used during formulation, while the concentration of nanoparticles was derived from the nominal particle size (i.e. particle volume of a sphere) and the amount of perfluorocarbon formulated into the preparation. The number of $Gd^{3+}$-complexes per nanoparticle was determined from the ratio of the concentrations of $Gd^{3+}$ and nanoparticles in the emulsion.

The nominal particle sizes and distributions of the Gd-DTPA-PE and Gd-DTPA-BOA nanoparticles were similar and overlapping, as shown in FIG. 1. Table 1 shows additional properties:

TABLE 1

Properties of Paramagnetic Nanoparticles.

|  | Gd-DTPA-BOA | Gd-DTPA-PE |
|---|---|---|
| Particle Size (nm) | 287 | 261 |
| Polydispersity Index | 0.28 | 0.23 |
| [$Gd^{3+}$] (mM) | 3.36 | 5.79 |
| $Gd^{3+}$ Ions/Particle | 56,900 | 73,600 |
| [Particles] (nM) | 59.1 | 78.7 |

Each lipophilic nanoparticle presented more than 50,000 Gd-complexes along the water-lipid interface. The capacity of these nanoparticles to support high paramagnetic payload is important to the efficacy of these agents when employed for molecular imaging of biochemical epitopes.

EXAMPLE 2

Paramagnetic Nanoparticle Sample Preparation and Assessment of $T_1$ and $T_2$ Relaxivities at 0.47 T, 1.5 T and 4.7 T Gd-DTPA-BOA and Gd-DTPA-PE nanoparticles prepared in Example 1 were diluted to 0, 4, 6, 8, 10 and 12% PFOB (v/v) with distilled deionized water. The initial nanoparticle formulation contained 26.1 mol/L $^{19}F$ and the diluted aliquots had 0, 3.915, 5.22, 6.525 and 7.83 mol/L $^{19}F$, respectively. Total gadolinium content was determined by neutron activation analysis. The gadolinium contents of the Gd-DTPA-BOA nanoparticle dilutions were 0; 0.336; 0.504; 0.672; 0.84; and 1.01 mmol/L $Gd^{3+}$. The paramagnetic ion concentrations in Gd-DTPA-PE samples were 0; 0.579; 0.869; 1.16; 1.45; and 1.74 mmol/L $Gd^{3+}$.

The proton longitudinal and transverse relaxation rates ($1/T_1$ and $1/T_2$, respectively) of each sample were measured at 40° C. on a Bruker MQ20 Minispec NMR Analyzer with a field strength of 0.47 T. $T_1$ was measured using an inversion recovery sequence with 10 inversion delay values, while $T_2$ was measured with a Carr-Purcell-Meiboom-Gill (CPMG) sequence. The $T_1$ and $T_2$ relaxivities (i.e., $\rho_1$ and $\rho_2$, respectively) were calculated from the slope of the linear least-squares regression of longitudinal and transverse relaxation rates versus $Gd^{3+}$ (i.e., ion relaxivity) or nanoparticle (i.e., particle relaxivity) concentrations and are reported in units of $(s*mM)^{-1}$.

Spin echo images from a clinical scanner (Gyroscan NT, PowerTrak 6000, Philips Medical Systems, Best, Netherlands) obtained with a standard 11 cm diameter surface coil were used to measure the relaxivity of the two nanoparticle formulations at 1.5 T. A six chamber phantom allowed all six dilutions to be studied in parallel. To accommodate the different relaxation times of the two paramagnetic formulations, different imaging parameters were applied. $T_1$ was calculated from an inversion recovery MRI pulse sequence. The measurement for the Gd-DTPA-BOA phantom included six inversion times ($T_1$) ranging from 50 to 1500 ms, while the Gd-DTPA-PE value utilized seven $T_1$ values ranging from 5 ms to 200 ms. The signal intensity (S1) from each chamber was fit to the equation:

$$S1_{TI} = S1_0 * (1 - EXP(-TI/T_1)), \qquad [1]$$

where $S1_0$ represents the equilibrium signal intensity. The $T_2$ value for Gd-DTPA-BOA was derived from a multi-echo sequence with 8 echo times (TE) ranging from 20 ms to 160 ms. Nine separate images with echo times ranging from 4.5 ms to 200 ms were used to calculate the $T_2$ relaxation for the Gd-DTPA-PE phantom. MRI signal intensity was fit to the equation:

$$S1_{TE} = S1_0 * EXP(-TE/T_2). \qquad [2]$$

The imaging parameters common for both formulations were: TR=1000 ms, TE=5 ms (unless otherwise noted), number of signal averages=4, image matrix=128 by 128, FOV=7 cm by 7 cm, flip angle=90°, slice thickness=5 mm.

The relaxivities of the two paramagnetic formulations were also measured with a 4.7 T magnet interfaced to a Varian INOVA console (Varian Associates, Palo Alto, Calif.) using a 5 cm birdcage coil. As stated earlier, a six chamber phantom was used to study the various emulsion dilutions concurrently. $T_1$ and $T_2$ values were obtained with inversion recovery (TE=7.2 ms, $T_1$ varied from 1 to 800 ms) and spin echo (TE varied from 7.2 to 100 ms) pulse sequences, respectively. The images were collected with TR=3000 ms, number of signal averages=4, image matrix=256 by 256, FOV=4 cm by 4 cm, flip angle=90°, slice thickness=2 mm.

Finally, the relaxivities of the two paramagnetic preparations were measured independently at magnetic fields ranging from 0.05 T to 1.3 T (2–56 MHz) using a custom built variable field relaxometer (Southwest Research Institute, San Antonio, Tex.). The samples were measured at temperatures of 3° and 37° C. A saturation recovery pulse sequence with 32 incremental τ values was used to measure $\rho_1$, while $\rho_2$ was measured using a CPMG pulse sequence with 500 echoes and a 2 ms inter-echo delay time.

Table 2 shows $T_1$ and $T_2$ relaxivities of the Gd-DTPA-BOA and Gd-DTPA-PE paramagnetic formulations determined at three magnetic field strengths.

TABLE 2

Relaxivities of Gd-DTPA-BOA and Gd-DTPA-PE emulsions at three different field strengths.

| Magnetic Field | Paramagnetic Chelate | Ion-Based Relaxivity $(s*mM)^{-1}$ | | Particle-Based Relaxivity $(s*mM)^{-1}$ | |
|---|---|---|---|---|---|
| | | $\rho_1$ | $\rho_2$ | $\rho_1$ | $\rho_2$ |
| 0.47 T | Gd-DTPA-BOA | 21.3 ± 0.2 | 23.8 ± 0.3 | 1,210,000 ± 10,000 | 1,350,000 ± 20,000 |
| | Gd-DTPA-PE | 36.9 ± 0.5 | 42.3 ± 0.6 | 2,710,000 ± 40,000 | 3,110,000 ± 50,000 |
| 1.5 T | Gd-DTPA-BOA | 17.7 ± 0.2 | 25.3 ± 0.6 | 1,010,000 ± 10,000 | 1,440,000 ± 30,000 |
| | Gd-DTPA-PE | 33.7 ± 0.7 | 50 ± 2 | 2,480,000 ± 50,000 | 3,700,000 ± 100,000 |
| 4.7 T | Gd-DTPA-BOA | 9.7 ± 0.2 | 29.4 ± 0.3 | 549,000 ± 9,000 | 1,670,000 ± 20,000 |
| | Gd-DTPA-PE | 15.9 ± 0.1 | 80 ± 0.7 | 1,170,000 ± 6,000 | 5,880,000 ± 50,000 |

At all magnetic field strengths, both the ion-based and particle-based $\rho_1$ of the Gd-DTPA-PE formulation were about two-fold greater (p<0.05) than $\rho_1$ of the Gd-DTPA-BOA agent. Similarly, ion-based and particle-based $\rho_2$ of the Gd-DTPA-PE agent were approximately two-fold higher (p<0.05) than $\rho_2$ of the Gd-DTPA-BOA system at the lowest magnetic field strength (0.47 T), and this relative difference was more than three-fold greater ($p<0.05$) at the highest field strength (4.7 T).

At 1.5 T, a typical medical imaging field strength, the ion-based $\rho_1$ and $\rho_2$ for Gd-DTPA-BOA were 17.7±0.2 $(s*mM)^{-1}$ (mean±standard error) and 25.3±0.6 $(s*mM)^{-1}$, respectively, consistent with our previous reported estimates (Flacke, S., et al., *Circulation* (2001) 104:1280–1285). Incorporation of Gd-DTPA-PE (as opposed to Gd-DTPA-BOA) increased the ion-based $\rho_1$ and $\rho_2$ to 33.7±0.7 $(s*mM)^{-1}$ and 50.0±2 $(s*mM)^{-1}$, respectively. More importantly from a targeted agent perspective, the particle-based $\rho_1$ and $\rho_2$ for Gd-DTPA-BOA were 1,010,000±10,000 $(s*mM)^{-1}$ and 1,440,000±30,000 $(s*mM)^{-1}$, respectively, and for Gd-DTPA-PE nanoparticles the particle-based $\rho_1$ and $\rho_2$ were 2,480,000±50,000 $(s*mM)^{-1}$ and 3,700,000±100,000 $(s*mM)^{-1}$, respectively. To our knowledge, particulate or molecular relaxivities in these ranges are the highest values reported to date for any targeted or blood pool paramagnetic contrast agent at these field strengths.

Figure 2:
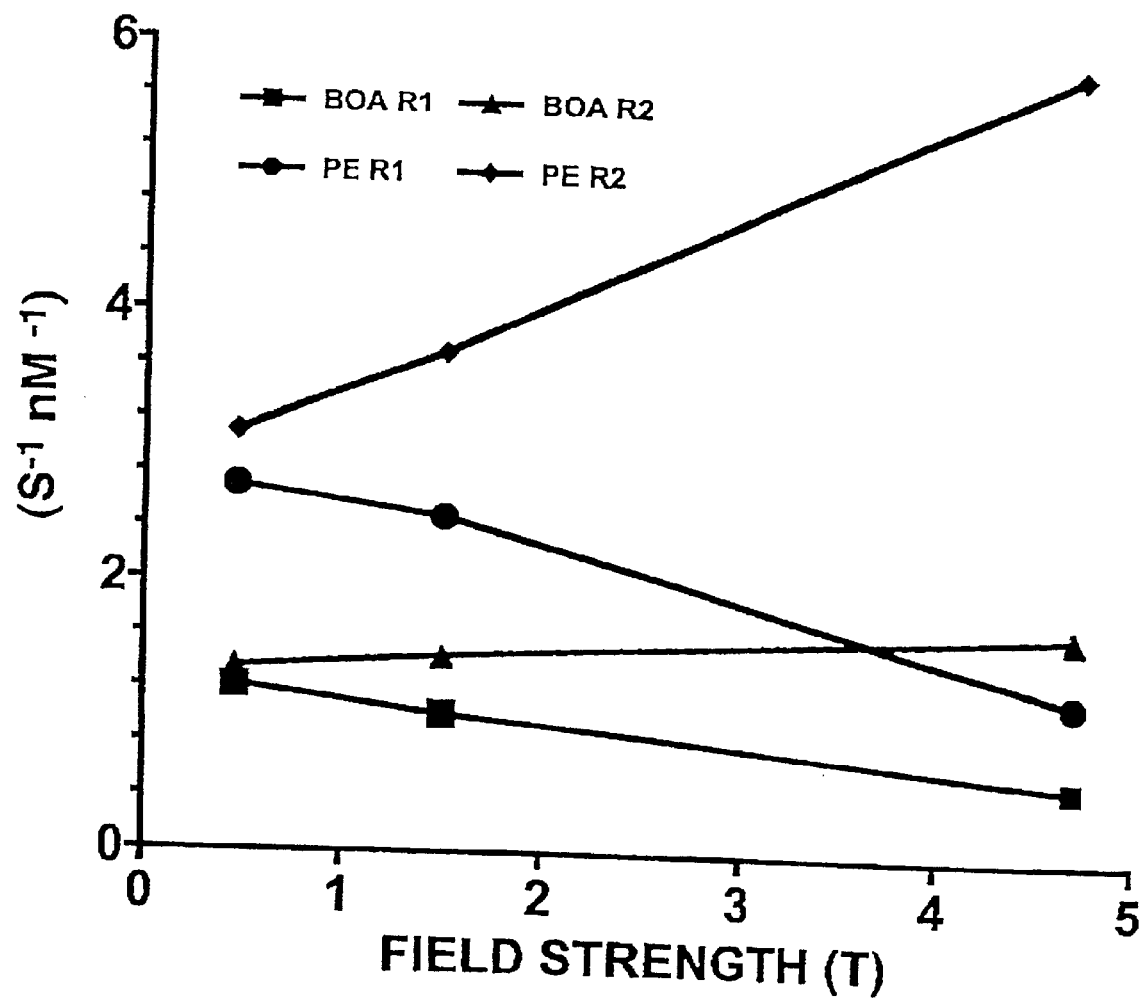
FIG. 2 is a graph showing the dependence of relaxivity for the surrounding hydrogen nuclei in units of $(s*mM)^{-1}$ for Gd-DTPA-BOA and Gd-DTPA-PE as a function of magnetic field strength.

The influence of magnetic field strength on relaxivity is shown in FIG. 2. The magnitudes of ion and particle longitudinal relaxivities declined as magnetic field strength increased from 0.47 T to 4.7 T, whereas the ion and particle transverse relaxivities progressively increased with higher field strengths. Although the particle longitudinal relaxivity declined about 50% at 4.7 T compared to 1.5 T, the particle $\rho_1$ remained very high. As a ligand-targeted contrast agent, the decreases in relaxivity at higher field strengths will be effectively offset by reduced voxel sizes, smaller partial volume dilution effects and improved signal to noise.

Figure 3:
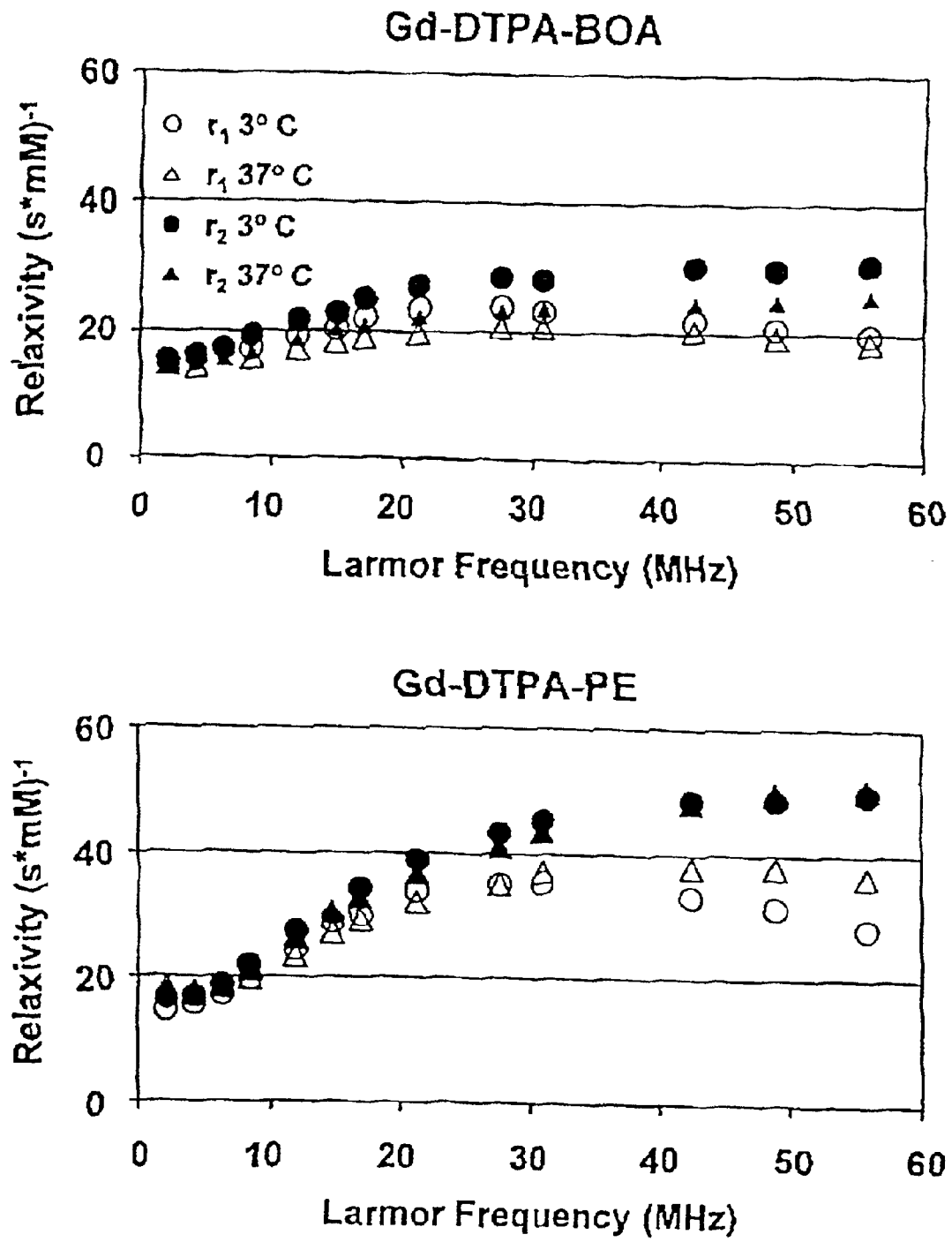
FIG. 3 shows the relaxivities of Gd-DTPA-BOA and Gd-DTPA-PE at 3° C. and 37° C. as a function of Larmor frequency in megahertz. (The Larmor frequency is the procession frequency of the energy-emitting nucleus.)

Variable field relaxometry measurements showed that $\rho_1$ of both emulsions was dominated by the long correlation time ($\tau_c$) of the slowly tumbling emulsion complex (FIG. 3). In fact, the particles were relatively so large, that there was almost no field dependence (dispersion). In contrast, the $\rho_2$ values initially followed those of $\rho_1$ but did not decrease at higher fields in accordance with expectations based on the Solomon-Bloembergen equations (Wood, M. L., *J. Mag. Res. Imag.* (1993) 3:149–156) (due to the non-dispersive term involving $\tau_c$). For the Gd-DTPA-BOA emulsion, the "peak" $\rho_1$ relaxivity was around 25 $(s*mM)^{-1}$ and the maximum value of $\rho_2$ was 30 $(s*mM)^{-1}$. The value of $\rho_1$ was largely independent of temperature, but $\rho_2$ increased at the lower temperature. For the Gd-DTPA-PE emulsion, however, the relaxivities were much higher, with $\rho_1$ reaching 40 $(s*mM)^{-1}$ at 40 MHz (approx 1.7 T) and $\rho_2$ reaching 50 $(s*mM)^{-1}$ at 56 MHz (1.3 T). The temperature dependence of Gd-DTPA-PE was also different from Gd-DTPA-BOA with $\rho_1$ decreasing at the lower temperature and $\rho_2$ remaining independent of temperature. The relaxometry values were consistent with analogous measurements made at 0.47 T and 1.5 T (Table 2). Moreover, the temperature dependence of these curves suggested that the Gd-DTPA-PE chelate has better access to water (i.e., faster exchange) compared to Gd-DTPA-BOA.

EXAMPLE 3

$^{19}$F Spectroscopy and Imaging

The $^{19}$F signal intensities of Gd-DTPA-BOA and Gd-DTPA-PE nanoparticles were characterized at 0.47 T and 4.7 T, but the necessary RF channel was unavailable for study at 1.5 T. At 0.47 T, $^{19}$F spectra were collected from each sample and the signal was quantified with respect to a reagent-grade PFOB standard. At 4.7 T, spin echo $^{19}$F images were collected from a six chamber phantom using a 1.5 cm single turn solenoid coil, dual-tuned to $^1$H and $^{19}$F. The imaging parameters were: TR=5000 ms, TE=6.3 ms, number of signal averages=35, image matrix=256 by 256, FOV=2 by 2 cm, flip angle=90°, slice thickness=1 mm. The relative $^{19}$F signal intensity of each chamber was determined from the image pixel grayscale using Scion Image (version: beta 3b) (Scion Corporation, Frederick, Md.).

Figure 4:
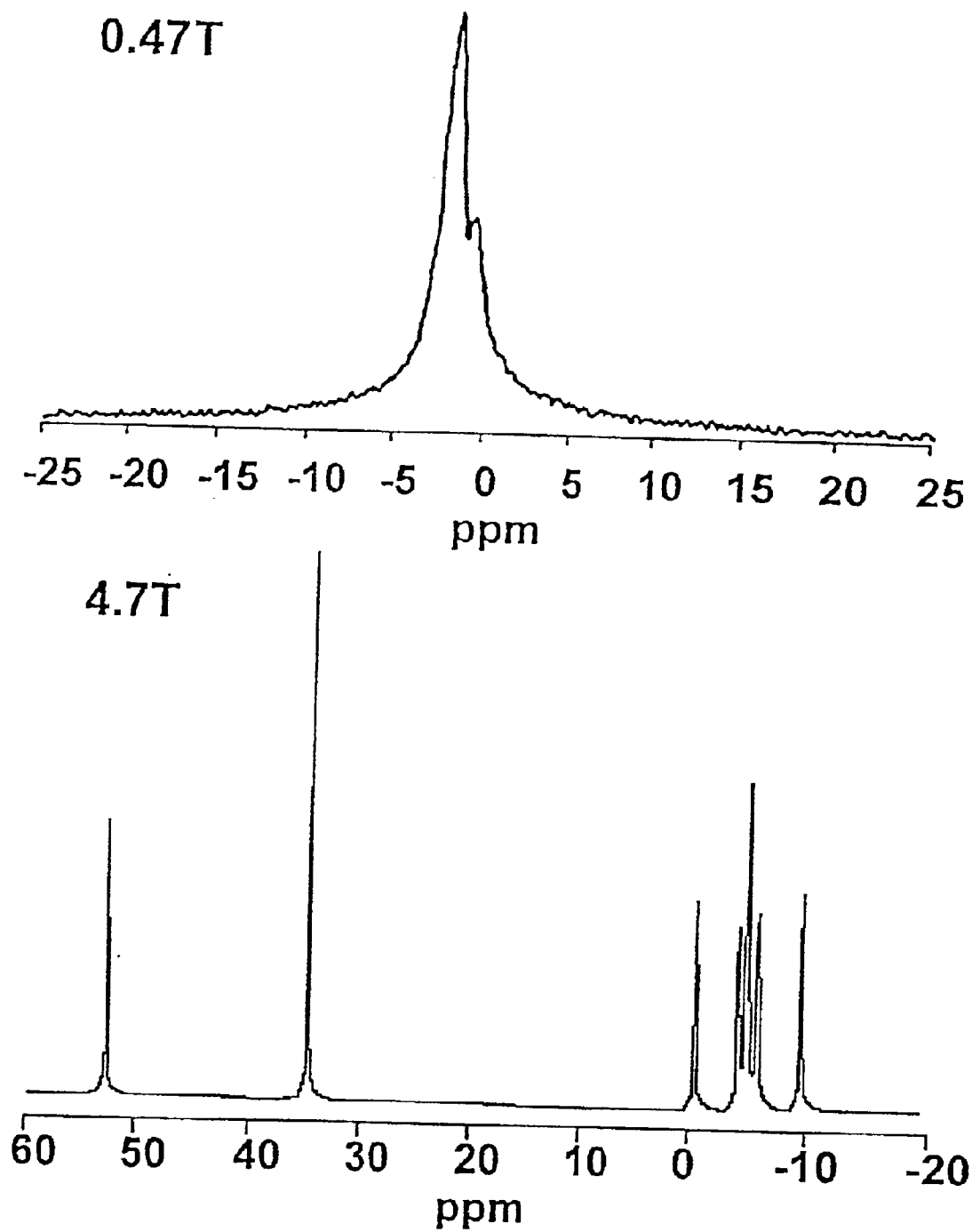
FIG. 4 shows sample $^{19}F$ spectra at 0.47 T and 4.7 T magnetic fields.
Figure 5:
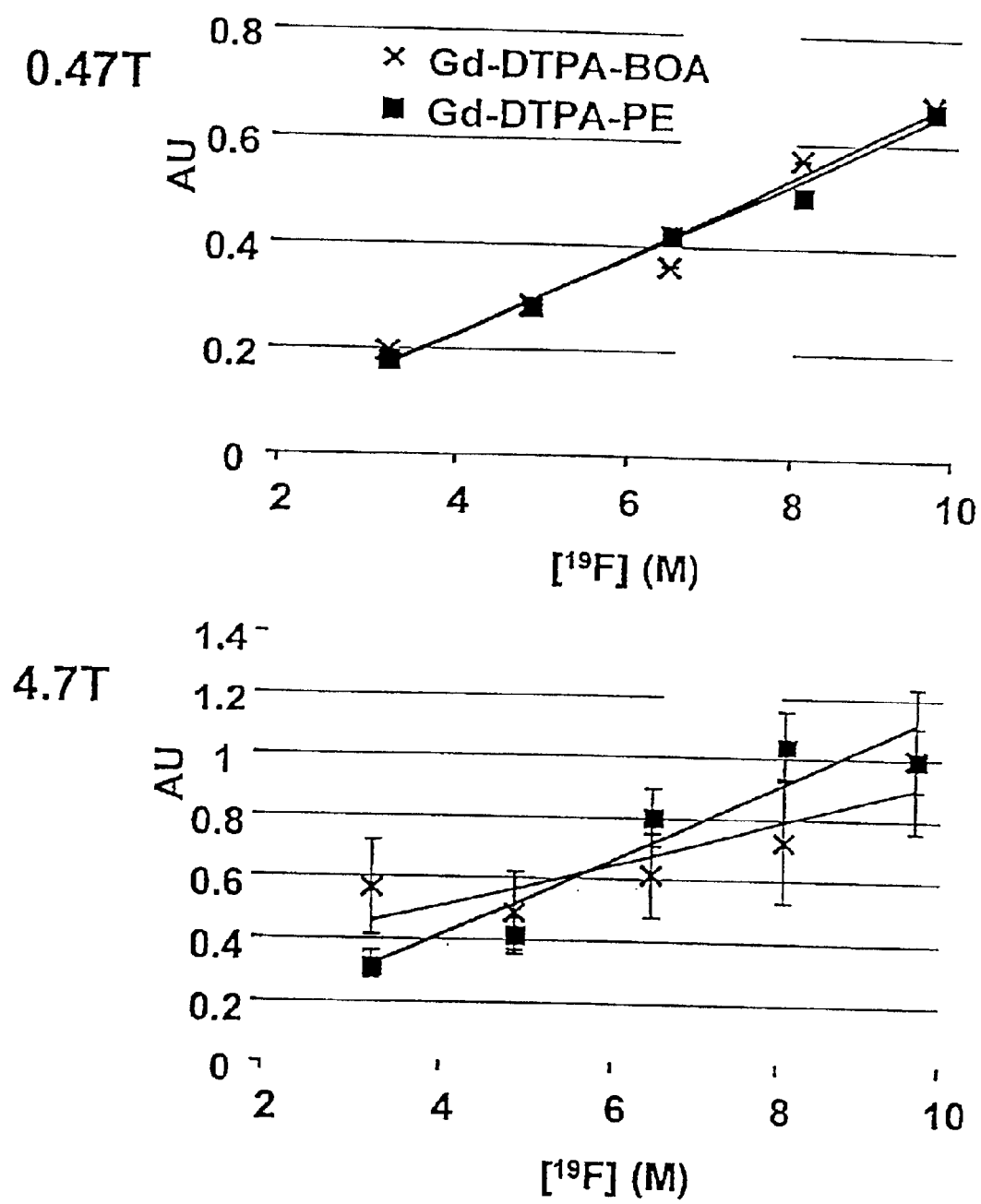
FIG. 5 shows the effect of $^{19}F$ concentration on $^{19}F$ signal intensity in the presence of emulsions of Gd-DTPA-BOA and Gd-DTPA-PE.

Representative fluorine spectra collected at 0.47 T and 4.7 T (FIG. 4) from the PFOB nanoparticle formulations revealed a markedly improved spectral resolution, as expected, at the higher field strength, which allows the multiple resonances of PFOB to be clearly separated. By comparison, these multiple resonance peaks collapsed into a single unsymmetrical resonance at 0.47 T equivalent to the integration of all PFOB resonances with improved signal to noise ratio. The $^{19}$F signal intensity of paramagnetic nanoparticles increased linearly with concentration at 0.47 T and 4.7 T independent of the lipophilic gadolinium chelate employed (FIG. 5). At 0.47 T, $^{19}$F signal intensities at each concentration of the two paramagnetic formulations were virtually superimposable, implying that the PFOB contents were nearly equivalent. At 4.7 T, $^{19}$F signal intensity estimates of the two paramagnetic nanoparticle formulations were more variable but statistically identical. The increased variation in measurements at the 4.7 T field strength was due to errors in signal intensity estimation secondary to chemical shift artifacts. Despite these issues, the amplitude of the fluorine signal was directly correlated with nanoparticle concentration.

Appendix—Typical Components

Typical Core Components

Among the perfluorocarbon compounds which may be employed are perfluorotributylamine (FC47), perfluorodecalin (PP5), perfluoromethyldecalin (PP9), perfluorooctylbromide, perfluorotetrahydrofuran (FC80), perfluroether (PID), [$(CF_3)_2CFOCF_2(CF_2)_2CF_2OCF(CF_3)_2$] perfluoroether (PIID) [$(CF_3)_2CFOCF_2(CF_2)_6CF_2OCF(CF_3)_2$], perfluoroetherpolymer (Fomblin Y/01), perfluorododecane, perfluorobicyclo[4.3.0.]nonane, perfluorotritrimethylbicyclohexane, perfluorotripropylamine, perfluoroisopropyl cyclohexane, perfluoroendotetrahydrodicyclopentadiene, perfluoroadamantane, perfluoroexotetrahydrodicyclopentadiene, perfluorbicyclo[5.3.0.]decane, perfluorotetramethylcyclohexane, perfluoro-1-methyl-4-isopropylcyclohexane, perfluoro-n-butylcyclohexane, perfluorodimethylbicyclo[3.3.1.]nonane, perfluoro-1-methyl adamantane, perfluoro-1-methyl-4-t butylcyclohexane, perfluorodecahydroacenapthane, perfluorotrimethylbicyclo[3.3.1.]nonane, perfluoro-1-methyl adamantane, perfluoro-1-methyl-4-t butylcyclohexane, perfluorodecahydroacenaphthene, perfluorotrimethylbicyclo[3.3.1.]nonane, perfluoronundecane, perfluorotetradecahydrophenanthrene, perfluoro-1,3,5,7-tetramethyladamantane, perfluorododecahydrofluorene, perfluoro-1-3-dimethyladamantane, perfluoro-n-octylcyclohexane, perfluoro-7-methyl bicyclo[4.3.0.]nonane, perfluoro-p-diisopropylcyclohexane, perfluoro-m-diisopropylcyclohexane, perfluoro-4-methyloctahydroquinolidizine, perfluoro-N-methyldecahydroquinoline, F-methyl-1-oxadecalin, perfluorooctahydroquinolidizine, perfluoro 5,6-dihydro-5-decene, perfluoro-4,5-dihydro-4-octene, perfluorodichlorooctane and perfluorobischlorobutyl ether, perfluorooctane, perfluorodichlorooctane, perfluoro-n-octyl bromide, perfluoroheptane, perfluorodecane, perfluorocyclohexane, perfluoromorpholine, perfluorotripropylamine, perfluortributylamine, perfluorodimethylcyclohexane, perfluorotrimethylcyclohexane, perfluorodicyclohexyl ether, perfluoro-n-butyltetrahydrofuran, and compounds that are structurally similar to these compounds. Chlorinated perfluorocarbons, such as chloroadamantane and chloromethyladamantane as described in U.S. Pat. No. 4,686,024 may be used. Such compounds are described, for example in U.S. Pat. Nos. 3,962,439; 3,493,581, 4,110,474, 4,186,253; 4,187,252; 4,252,824; 4,423,077; 4,443,480; 4,534,978 and 4,542,147.

Surfactants

Commercially available surfactants are Pluronic F-68, Hamposyl™ L30 (W.R. Grace Co., Nashua, N.H.), sodium dodecyl sulfate, Aerosol 413 (American Cyanamid Co., Wayne, N.J.), Aerosol 200 (American Cyanamid Co.), Lipoproteol™ LCO (Rhodia Inc., Mammoth, N.J.), Standapol™ SH 135 (Henkel Corp., Teaneck, N.J.), Fizul™ 10-127 (Finetex Inc., Elmwood Park, N.J.), and Cyclopol™ SBFA 30 (Cyclo Chemicals Corp., Miami, Fla.); amphoterics, such as those sold with the trade names: Deriphat™ 170 (Henkel Corp.), Lonzaine™ JS (Lonza, Inc.), Niranol™ C2N-SF (Miranol Chemical Co., Inc., Dayton, N.J.), Amphoterge™ W2 (Lonza, Inc.), and Amphoterge™ 2WAS (Lonza, Inc.); non-ionics, such as those sold with the trade names: Pluronic™ F-68 (BASF Wyandotte, Wyandotte, Mich.), Pluronic™ F-127 (BASF Wyandotte), Brij™ 35 (ICI Americas; Wilmington, Del.), Triton™ X-100 (Rohm and Haas Co., Philadelphia, Pa.), Brij™ 52 (ICI Americas), Span™ 20 (ICI Americas), Generol™ 122 ES (Henkel Corp.), Triton™ N-42 (Rohm and Haas Co.), Triton™ N-101 (Rohm and Haas Co.), Triton™ X-405 (Rohm and Haas Co.), Tween™ 80 (ICI Americas), Tween™ 85 (ICI Americas), and Brij™ 56 (ICI Americas) and the like.

Also included may be egg yolk phospholipids, alkylphosphoryl choline or alkylglycerolphosphoryl choline surfactants, and specific examples of these such as 1,2-dioctylglycero-3-phosphoryl choline, 1,2-ditetradecylglycero-3-phosphoryl choline, 1,2-dihexadecylglycero-3-phosphoryl choline, 1,2-dioctadecylglycero-3-phosphorylcholine, 1-hexadecyl-2-tetradecylglycero-3-phosphoryl choline, 1-octadecyl-2-tetradecylglycero-3-phosphoryl choline, 1-tetradecyl-2-octadecylglycero-3-phosphoryl choline, 1-hexadecyl-2-octadecylglycero-3-phosphoryl choline, 1-2-dioctadecylglycero-3-phosphoryl choline, 1-octadecyl-2-hexadecylglycero-3-phosphoryl choline, 1-tetradecyl-2-hexadecylglycero-3-phosphoryl choline, 2,2-ditetradecyl-1-phosphoryl choline ethane and 1-hexadecyltetradecylglycero-3-phosphoryl choline.

Suitable perfluorinated alcohol phosphate esters include the free acids of the diethanolamine salts of mono- and bis(1H,1H,2H,2H-perfluoroalkyl)phosphates. The phosphate salts, available under the trade name "Zonyl RP" (E.I. Dupont de Nemours and Co., Wilmington, Del.), are converted to the corresponding free acids by known methods. Suitable perfluorinated sulfonamide alcohol phosphate esters are described in U.S. Pat. No. 3,094,547. Suitable perfluorinated sulfonamide alcohol phosphate esters and salts of these include perfluoro-n-octyl-N-ethylsulfonamidoethyl phosphate, bis(perfluoro-n-octyl-N-ethylsulfonamidoethyl)phosphate, the ammonium salt of bis(perfluoro-n-octyl-N-ethylsulfonamidoethyl)phosphate, bis(perfluoro-decyl-N-ethylsulfonamidoethyl)-phosphate and bis(perfluorohexyl-N ethylsulfonamidoethyl)-phosphate. The preferred formulations use phosphatidylcholine, derivatized-phosphatidylethanolamine and cholesterol as the aqueous surfactant.

Illustrative Bioactive Agents

Biologically active molecules which may be included and coupled to the coating include antineoplastic agents, such as platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, taxol, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwina asparaginase, etoposide (VP-16), interferon α-2a, interferon α-2b, teniposide (VM-26), vinblastine sulfate (VLB), vincristine sulfate, bleomycin, bleomycin sulfate, methotrexate, adriamycin, arabinosyl, hydroxyurea, procarbazine, and dacarbazine; mitotic inhibitors such as etoposide and the vinca alkaloids, radiopharmaceuticals such as radioactive iodine and phosphorus products; hormones such as progestins, estrogens and antiestrogens; anti-helmintics, antimalarials, and antituberculosis drugs; biologicals such as immune serums, antitoxins and antivenins; rabies prophylaxis products; bacterial vaccines; viral vaccines; aminoglycosides; respiratory products such as xanthine derivatives theophylline and aminophylline; thyroid agents such as iodine products and anti-thyroid agents; cardiovascular products including chelating agents and mercurial diuretics and cardiac glycosides; glucagon; blood products such as parenteral iron, hemin, hematoporphyrins and their derivatives; biological response modifiers such as muramyldipeptide, muramyltripeptide, microbial cell wall components, lymphokines (e.g., bacterial endotoxin such as lipopolysaccharide, macrophage activation factor), subunits of bacteria (such as *Mycobacteria, Corynebacteria*), the synthetic dipeptide N-acetyl-muramyl-L-alanyl-D-isoglutamine; anti-fungal agents such as ketoconazole, nystatin, griseofulvin, flucytosine (5-fc), miconazole, amphotericin B, ricin, cyclosporins, and β-lactam antibiotics (e.g., sulfazecin); hormones such as growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, and their derivatives; vitamins such as cyanocobalamin neinoic acid, retinoids and derivatives such as retinol palmitate, and α-tocopherol; peptides, such as manganese super oxide dismutase; enzymes such as alkaline phosphatase; anti-allergic agents such as amelexanox; anti-coagulation agents such as phenprocoumon and heparin; circulatory drugs such as propranolol; metabolic potentiators such as glutathione; antitubercular such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT, DDI, Foscarnet, or Zidovudine), ribavirin and vidarabine monohydrate (adenine arabinoside, ara-A); anti-anginals such as diltiazem, nifedipine, verapamil, erythritol tetranitrate, isosorbide dinitrate, nitroglycerin (glyceryl trinitrate) and pentaerythritol tetranitrate; anticoagulants such as phenprocoumon, heparin; antibiotics such as dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin and tetracycline; antiinflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric;opiates such as codeine, heroin, methadone, morphine and opium; cardiac glycosides such as deslanoside, digitoxin, digoxin, digitalin and digitalis; neuromuscular blockers such as atracurium mesylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; general anesthetics such as droperidol, etomidate, fentanyl citrate with droperidol, ketamine hydrochloride, methohexital sodium and thiopental sodium; and radioactive particles or ions such as strontium, iodide rhenium and yttrium.

What is claimed is:

1. A contrast agent for magnetic resonance imaging (MRI), which agent comprises particles, wherein said particles are coupled to a chelator containing a paramagnetic ion which ion is positioned offset from the surface of the particles, so as to provide said ion substantial access to hydrogen nuclei in a surrounding liquid, whereby the relaxivity of said nuclei is enhanced, wherein said particles are microparticles or nanoparticles comprised of an inert core comprising fluorocarbon liquid surrounded by a lipid/surfactant coating, and wherein said offset is such that the particle provides a $\rho_1$ of at least about $0.5 \times 10^6$ $(s^*mM)^{-1}$ or a $\rho_2$ of at least about $1 \times 10^6$ $(s^*mM)^{-1}$ at a field strenth of 1.5 T on a per particle basis;

and wherein the particles are emulsified in a liquid emulsion.

2. The agent of claim 1, wherein said offset is such that the particle provides a $\rho_1$ of at least about 10 $(s^*mM)^{-1}$ or a $\rho_2$ of at least about 20 $(s^*mM)^{-1}$ at a field strength of 1.5 T on a per ion basis.

3. The agent of claim 1, wherein said offset is such that $\rho_1$ is increased at least about 1.5-fold or $\rho_2$ is increased at least about 1.5-fold at a field strength of 1.5 T on a per particle basis as compared to $\rho_1$ or $\rho_2$ of particles wherein the paramagnetic ion resides at less than 5 Å from the surface.

4. The agent of claim 1, wherein said inert core comprises a perfluorocarbon compound.

5. The agent of claim 4, wherein the inert core comprises a mixture of fluorocarbons and oils.

6. The agent of claim 1, wherein the chelator is selected from the group consisting of a porphyrin, ethylenediaminetetraacetic acid (EDTA), diethylenetriamine-N,N,N',N'',N''-pentaacetate (DTPA), 1,4,10,13-tetraoxa-7,16-diazacyclooctadecane-7,16-diacetate, N-2-(azol-1(2)-yl)ethyliminodiacetic acid, 1,4,7,10-tetraazacyclododecane-N,N',N'',N'''-tetraacetic acid, 1,7,13-triaza-4,10,16-trioxacyclo-octadecane-N,N',N''-triacetate, tetraethylene glycol,1,5,9-triazacyclododecane-N,N',N'',-tris(methylene) phosphonic acid, and N,N',N''-trimethylammonium chloride.

7. The agent of claim 6, wherein the chelator is DTPA.

8. The agent claim 1, wherein the paramagnetic ion is selected from the group consisting of scandium, titanium, vanadium, chromium, manganese, iron, cobalt, nickel, copper, molybdenum, ruthenium, cerium, praseodymium, neodymium, promethium, samarium, europium, gadolinium, terbium, dysprosium, holmium, erbium, thulium, and ytterbium.

9. The agent of claim 8, wherein the paramagnetic ion is gadolinium.

10. The agent of claim 1, wherein the lipid/surfactant coating comprises at least one compound selected from the group consisting of a natural phospholipid, a synthetic phospholipid, a fatty acid, a cholesterol, a lysolipid, a sphingomyelin, a tocopherol, a glucolipid, a stearylamine, a cardiolipin, a lipid with an ether-linker fatty acid, a lipid with an ester linked fatty acid, a polymerized lipid, and a polyethylene glycol-conjugated lipid.

11. The agent of claim 1 wherein said particles are coupled to at least 10,000 chelators per particle.

12. The agent of claim 1, wherein said particles further comprise a coupled target-specific ligand.

13. The agent of claim 12, wherein said target specific ligand is an antibody, an antibody fragment, a peptide, an aptamer, a peptide mimetic, a drug or a hormone.

14. The agent of claim 13, wherein said target specific ligand is an antibody or fragment of an antibody.

15. The agent of claim 14, wherein said antibody is humanized and/or is a single chain $F_v$ antibody.

16. The agent of claim 12, wherein said particles comprise at least about 2 copies of said target-specific ligand per particle.

17. The agent of claim 12, wherein said target-specific ligand is coupled directly to said particles.

18. The agent of claim 1, wherein said particles further comprise a biological agent.

19. A method for magnetic resonance imaging (MRI), which method comprises administering the agent of claim 1 to a subject, permitting said agent to accumulate at a site of said subject for which an image is desired; and detecting an image of said site generated by hydrogen nuclei at said site.

20. The method of claim 19, wherein said site comprises a specific binding partner for a ligand, and wherein said particles further are coupled to a ligand specific for said specific binding partner.

21. A method for magnetic resonance imaging (MRI), which method comprises administering the agent of claim 4 to a subject, permitting said agent to accumulate at a site of said subject for which an image is desired; and detecting an image of said site generated by hydrogen nuclei at said site.

22. The method of claim 21, wherein said site comprises a specific binding partner for a ligand, and wherein said particles further are coupled to a ligand specific for said specific binding partner.

23. The method of claim 21, which further comprises detecting an image generated by $^{19}$F contained in said particles at said site.

24. The method of claim 22, which further comprises detecting an image generated by $^{19}$F contained in said particles at said site.

* * * * *